(12) United States Patent
Nobles et al.

(10) Patent No.: US 10,335,141 B2
(45) Date of Patent: Jul. 2, 2019

(54) VARIABLE SPREAD SUTURING DEVICE

(71) Applicant: HeartStitch, Inc., Fountain Valley, CA (US)

(72) Inventors: Anthony Nobles, Fountain Valley, CA (US); Steffen Schindler, Glauchau (DE)

(73) Assignee: HeartStitch, Inc., Fountain Valley, CA (US)

( * ) Notice: Subject to any disclaimer, the term of this patent is extended or adjusted under 35 U.S.C. 154(b) by 232 days.

(21) Appl. No.: 15/392,158

(22) Filed: Dec. 28, 2016

(65) Prior Publication Data

US 2017/0164944 A1 Jun. 15, 2017

Related U.S. Application Data

(63) Continuation of application No. 15/134,197, filed on Apr. 20, 2016, now Pat. No. 9,554,792.

(60) Provisional application No. 62/267,836, filed on Dec. 15, 2015.

(51) Int. Cl.
*A61B 17/04* (2006.01)
*A61B 17/06* (2006.01)
*A61B 17/062* (2006.01)

(52) U.S. Cl.
CPC ...... *A61B 17/0482* (2013.01); *A61B 17/0469* (2013.01); *A61B 17/062* (2013.01); *A61B 17/06004* (2013.01); *A61B 2017/0472* (2013.01); *A61B 2017/06042* (2013.01)

(58) Field of Classification Search
CPC ............ A61B 17/0469; A61B 17/0482; A61B 2017/047; A61B 2017/0472
See application file for complete search history.

(56) References Cited

U.S. PATENT DOCUMENTS

| | | |
|---|---|---|
| 5,374,275 A | 12/1994 | Bradley et al. |
| 5,507,755 A | 4/1996 | Gresl et al. |
| 5,507,757 A | 4/1996 | Sauer et al. |
| 5,527,321 A | 6/1996 | Hinchliffe |
| 5,630,825 A | 5/1997 | de la Torre et al. |
| 5,662,664 A | 9/1997 | Gordon et al. |
| 5,836,956 A | 11/1998 | Buelna et al. |

(Continued)

FOREIGN PATENT DOCUMENTS

WO 2015002815 A1 1/2015

OTHER PUBLICATIONS

International Search Report and Written Opinion for International Application No. PCT/US2016/066880 dated Apr. 5, 2017, 13 pages.

*Primary Examiner* — Julian W Woo
(74) *Attorney, Agent, or Firm* — Fish IP Law, LLP

(57) ABSTRACT

A suturing device, and methods for suturing various sizes of apertures in tissues, are presented. The suturing device has a body with at least one or more adjustable arms that are coupled with catch targets. The arms are coupled with needle guides such that movements of the arms orient the needle guides to direct the needles towards the catch targets. The catch targets are coupled with sutures, such that when the needles reach the targets, they capture and pull the sutures back to the body. By changing the angles at which the arms extend from the body, the catch targets are moved closer to, or farther from, the body, and the suture device is readily configured to suture various sizes of apertures.

17 Claims, 7 Drawing Sheets

(56) References Cited

U.S. PATENT DOCUMENTS

| | | | |
|---|---|---|---|
| 5,846,253 A | 12/1998 | Buelna et al. | |
| 6,117,144 A | 9/2000 | Nobles et al. | |
| 7,226,467 B2 * | 6/2007 | Lucatero | A61M 25/0136 |
| | | | 606/213 |
| 7,449,024 B2 | 11/2008 | Stafford | |
| 7,462,188 B2 * | 12/2008 | McIntosh | A61B 17/0469 |
| | | | 606/144 |
| 8,597,309 B2 | 12/2013 | Stafford | |
| 8,679,136 B2 | 3/2014 | Mitelberg | |
| 8,709,020 B2 | 4/2014 | Nobles | |
| 9,095,319 B2 | 8/2015 | Argentine | |
| 9,155,535 B2 | 10/2015 | McIntosh | |
| 9,554,792 B1 * | 1/2017 | Nobles | A61B 17/0469 |
| 2003/0028201 A1 * | 2/2003 | Navarro | A61B 17/0057 |
| | | | 606/139 |
| 2011/0190793 A1 | 8/2011 | Nobles et al. | |
| 2014/0128887 A1 | 5/2014 | Argentine | |

\* cited by examiner

VARIABLE SPREAD SUTURING DEVICE

This application is a continuation application of U.S. patent application Ser. No. 15/134,197, filed Apr. 20, 2016, now U.S. Pat. No. 9,554,792, which claims the benefit of priority to U.S. Provisional Patent Application No. 62/267,836, filed Dec. 15, 2015, all of which are incorporated by reference herein in its entirety.

FIELD OF THE INVENTION

The field of the invention is systems and method for suturing various sizes of apertures.

BACKGROUND

The background description includes information that may be useful in understanding the present invention. It is not an admission that any of the information provided herein is prior art or relevant to the presently claimed invention, or that any publication specifically or implicitly referenced is prior art.

Health practitioners frequently use sutures to close various openings such as cuts, punctures, and incisions in various places in the human body. Depending on types and sizes of tissues to be sutured, and their locations, various different types of needles, suture threads, and suture devices can be used in the suturing process. Also, the size of the wound or apertures that can be sutured by a suturing device is often limited by a size or a radius of a needle, or the distance from the needle to the needle capture device. Thus, most of currently available suturing device are directed to a specific size of wounds or apertures, and are unsuitable for suturing a range of different sizes of wounds or apertures.

There are suturing devices that can adapt to different sizes of wounds or apertures by deploying needles at different distances from the body of the device. For example, U.S. Pat. No. 5,374,275 to Bradley discloses a suturing device having a needle platform, which enables the physician/operator/user to use hinged connectors to deploy a needle by desired incremental distances from the body of the device. Similarly, U.S. Pat. No. 7,449,024 to Stafford discloses a suture device having split, movable arms, wherein each of the arms is coupled with one needle. Stafford's arms are independently movable at different angles. For another example, U.S. Pat. No. 8,709,020 to Nobles discloses a suture device having suture clasp members, which can be hinged in different angles. For yet another example, U.S. Pat. No. 5,507,757 to Sauer discloses a trocar wound closure device having laterally deployable needle holders. The number of retractable needle holders can be increased to make them suitable for closing large trocar wounds.

Yet, none of prior arts allows the needles moving in different angles toward a target which retains suture threads, so-called "throw and catch" suturing.

All publications identified herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

Thus, there is still a need for improved systems and methods for suturing various sizes of apertures.

SUMMARY OF THE INVENTION

The inventive subject matter provides systems and methods for suturing various sizes of apertures.

One aspect of the invention includes an adjustable suturing device for suturing various sizes of apertures. The device includes a body having an arm, and a catch target disposed in the arm such that movement of the arm moves the target away from the body. The arm is coupled to a needle guide such that the movement of the first arm orients the needle guide to direct the needle towards the catch target.

Another aspect of the invention includes methods of suturing various sizes of apertures. The methods include a step of providing a suture device having a body, one or more arms, and both a catch target and a needle guide coupled to each of the arms. The methods further include a step of moving an arm way from the body of the device at a desired angle, such that movement of the arm moves the target away from the body, and orients the needle guide to direct the needle towards the catch target.

Various objects, features, aspects and advantages of the inventive subject matter will become more apparent from the following detailed description of preferred embodiments, along with the accompanying drawing figures in which like numerals represent like components.

DETAILED DESCRIPTION

Figure 1A:
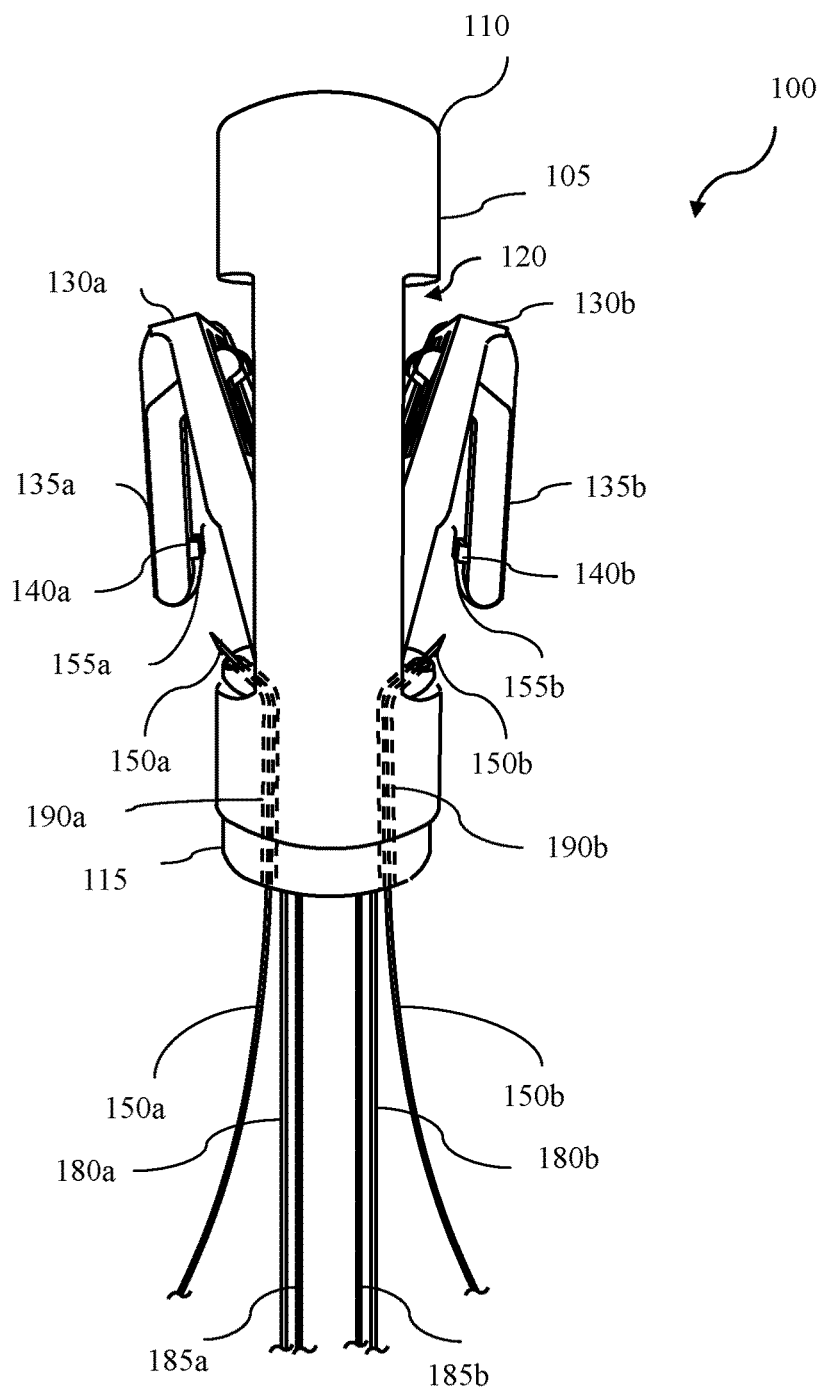
FIG. 1A illustrates a perspective view of an embodiment of the distal portion of suturing device in a partially closed configuration.

The inventive subject matter provides suturing devices, especially for suturing various sizes of apertures in tissues, and methods of suturing the apertures using the suturing devices.

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

In some embodiments, the numbers expressing quantities or ranges, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements. Unless the context dictates the contrary, all ranges set forth herein should be interpreted as being inclusive of their endpoints and open-ended ranges should be interpreted to include only commercially practical values. Similarly, all lists of values should be considered as inclusive of intermediate values unless the context indicates the contrary.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

All methods described herein can be performed in any suitable order unless otherwise indicated herein or otherwise clearly contradicted by context. The use of any and all examples, or exemplary language (e.g., "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

One aspect of the inventive subject matter includes a suturing device, especially a suturing device that is configurable to suture various sizes of apertures. The suturing device has a body that includes a lumen within which are disposed arm control elements and needles. The body is coupled with at least one arm, preferably two or more arms, each of which is coupled to a catch target. In a preferred embodiment, the arm is coupled with a needle guide.

For purposes of the present application, the term "needle" means both a length of metal or other material intended to pass through a tissue, along with an extension portion that can be used to direct translational or other motion of the working end of the needle. Thus, as used herein, a needle would typically be longer than the lumen of a catheter or trocar in which the needle is to be utilized. The length of needles can vary depending on the use of the suture device. For endoscopic suturing via vascular structures, it is preferred that lengths of needles are at least 10 cm, preferably at least 20 cm, and in at least some embodiments, more preferably at least 30 cm.

Figure 1B:
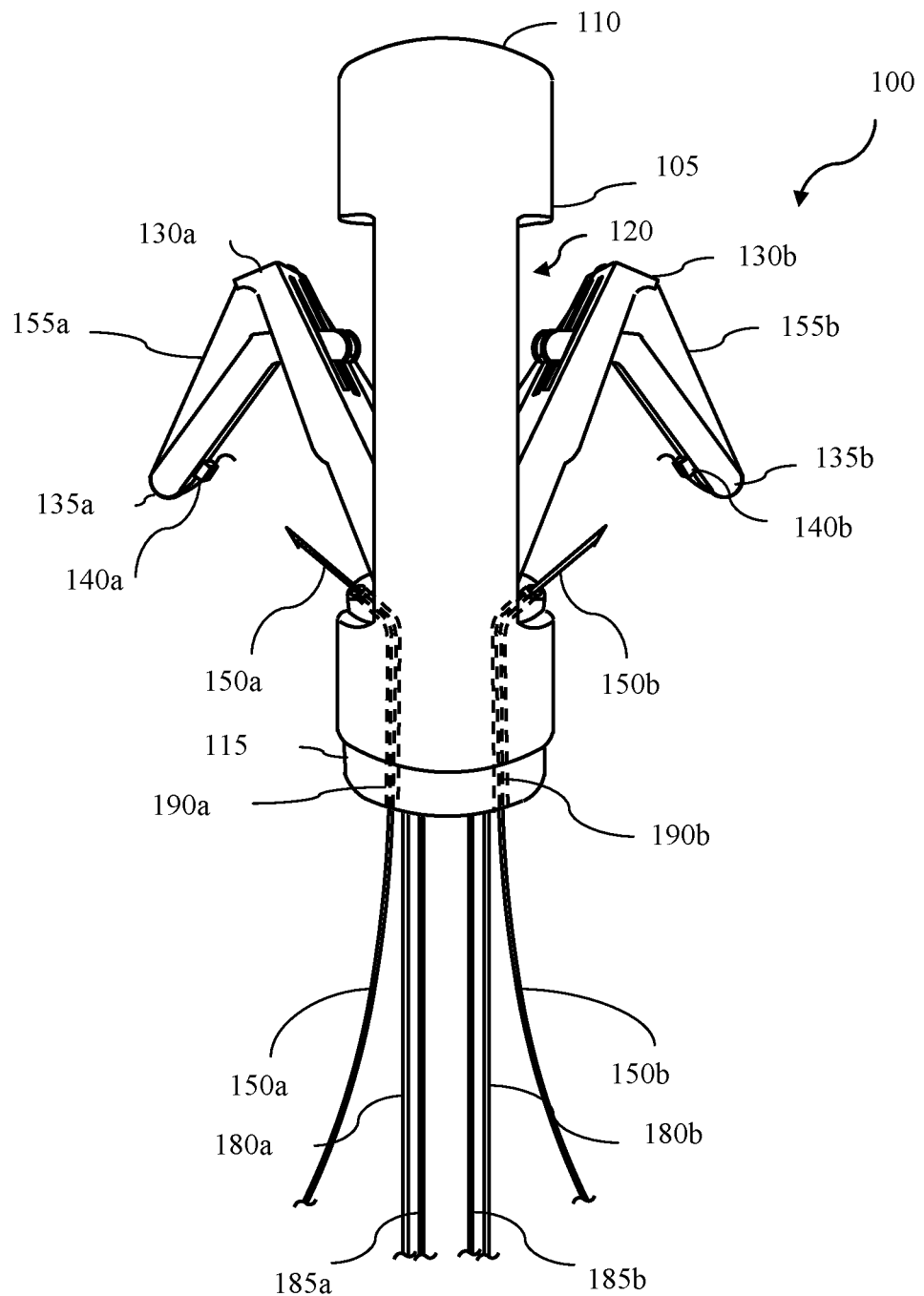
FIG. 1B illustrates a perspective view of the distal portion of suturing device of FIG. 1A in a partially open configuration.
Figure 1C:
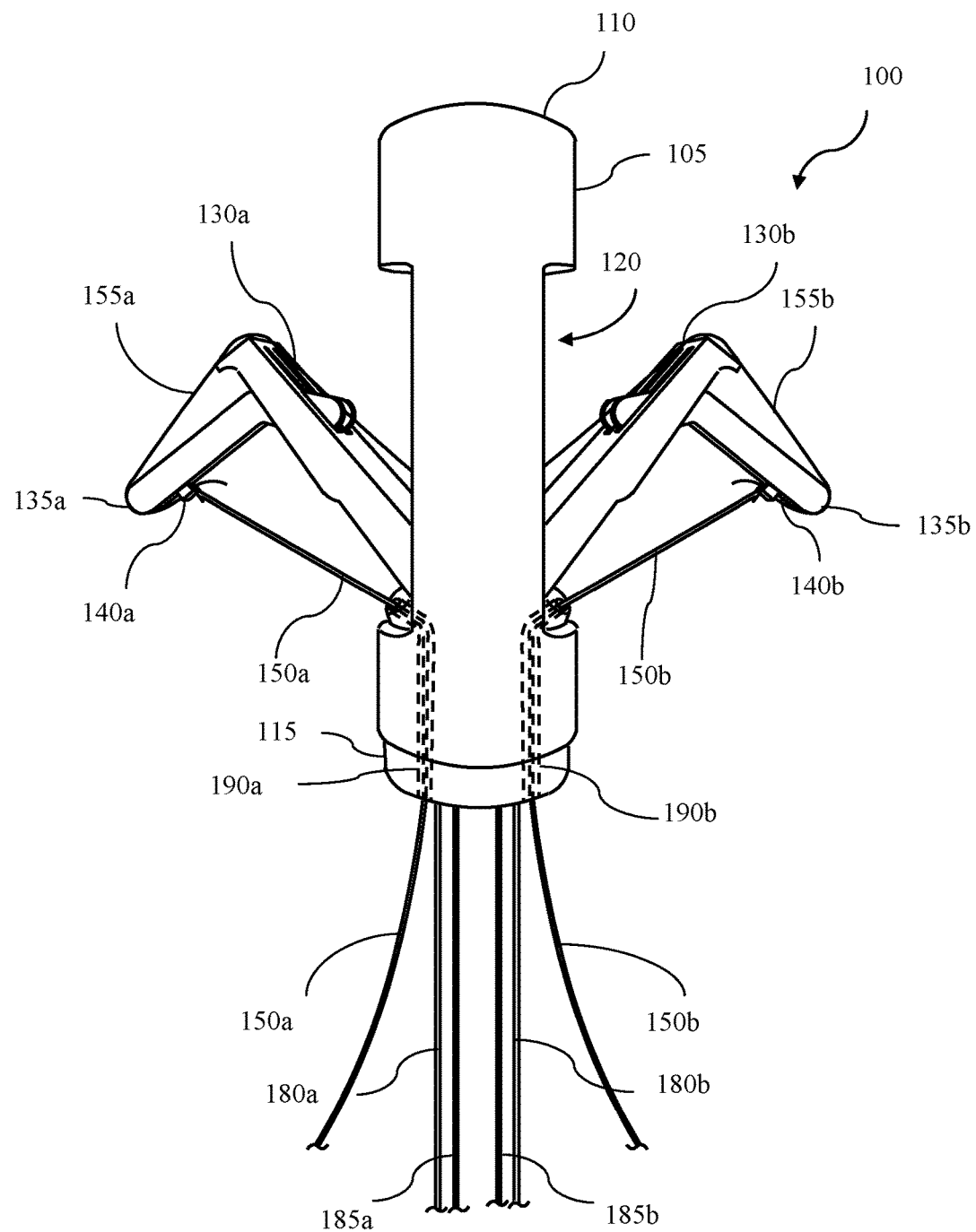
FIG. 1C illustrates a perspective view of the distal portion of suturing device of FIGS. 1A and 1B in a more open configuration.
Figure 2:
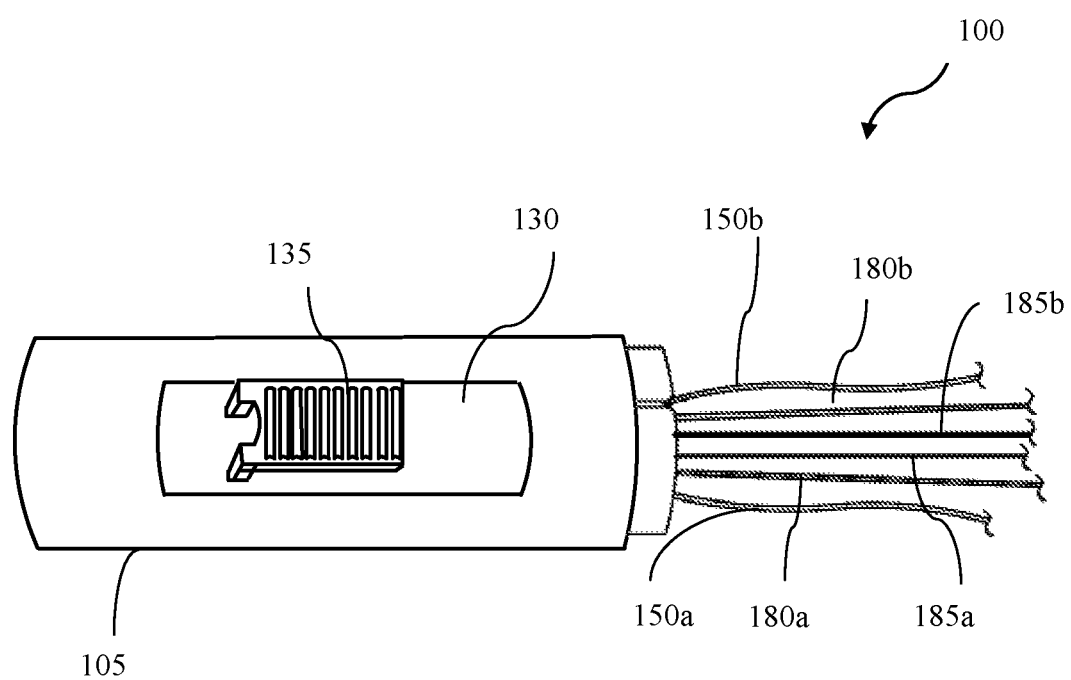
FIG. 2 illustrates a side view of the distal portion of suturing device of FIGS. 1A-C in a fully closed configuration.

FIGS. 1A-C illustrate an embodiment of a distal portion of suturing device 100 in a partially closed configuration FIG. 1A, in a partially open configuration FIG. 1B, and in a more open configuration FIG. 1C, respectively. FIG. 2 illustrates the distal portion of suturing device 100 of FIGS. 1A-C in a closed configuration. The distal portion of suturing device 100 has a body 105 with a lumen 120. As depicted in FIGS. 1A-C and 2, the body 105 can have a cylindrical shape. But these figures should be interpreted to indicate a body having any shape suitable for inserting into a body cavity, vascular or other structure. For example, the body can be in a cuboid shape, a triangular prism shape, a corn shape, a pyramid shape, or a prism shape.

Body 105 can comprise any suitable material or materials. For example, the body 105 can be made of one or more of plastic materials (e.g., polypropylene, polyethylene, nylon, PVC or PTFE), metal materials (e.g., aluminum, copper, platinum, metal alloys, etc.), silicon, or glass fiber. In some embodiments, the body 105 can be in biocompatible material.

When the distal portion of suturing device 100 is in a closed configuration as shown in FIG. 2, the arms 130a, 130b are substantially co-planar with a plane running longitudinally through the body 105. The body 105 is pivotally (hingeably) coupled with one or more arms 130a, 130b, by one or more pivots, such that the arms 130a, 130b can pivot laterally away from the body 105. It is contemplated that such lateral pivoting can occur by at least 45 degrees, preferably at least 90 degrees, and more preferably by at least 135 degrees.

In some embodiments where the body 105 is coupled with two arms 130a, 130b, the two arms 130a, 130b are preferably disposed to be deployed in opposite directions. In other embodiments where the body 105 is coupled with more than two arms, the arms are preferably arrayed evenly about the perimeter of the body 105. For example, if there are three arms coupled with the body 105, the three arms are preferably located in every 120 degree about the body in a circle. For other example, if there are four arms coupled with the body 105 and the body is in a cuboid shape, each of the four arms can be located in four different faces of the cuboid.

In a preferred embodiment, the arms 130a, 130b are coupled with one or more second arms 135a, 135b having proximal ends and distal ends. The proximal ends of the second arms 135a, 135b are coupled with the arm's distal ends by one or more pivots such that the second arms 135a, 135b can laterally moveable from the body 105 and from the arms 130a, 130b. It is contemplated that the second arms 135a, 135b can laterally moveable from the arm 130a, 130b at least 15 degrees, preferably at least 30 degrees, more preferably at least 45 degrees, and most preferably at least 90 degrees.

The second arms 135a, 135b includes a catch target 140a, 140b at their distal ends. The catch targets 140a, 140b position sutures 155a, 155b, respectively, so that needles 150a, 150b can approach the corresponding catch targets 140a, 140b and grab the sutures 155a, 155b. The catch targets can have any suitable shape(s) for grabbing or coupling with the sutures 155a, 155b. For example, the catch target can be in a clip shape, a curved pin shape, a hook shape, a loop shape.

Needles 150a, 150b are coupled with needle guides 190a, 190b, which direct the needles 150a, 150b towards the catch targets 140a, 140b. In a preferred embodiment, needle guides 190a, 190b are coupled with arms 130a, 130b, respectively, so that the movements of the needle guides 190a, 190b coordinate with movement of the arms 130a, 130b. For example, both the needle guides 190a, 190b and the arms 130a, 130b can be coupled using a common pole or stem (not shown) in the lumen 120 of the distal portion of suturing device 100. In another example, the needle guides 190a, 190 can be directly attached to lower portions of the arms 130a, 130b, respectively.

In FIGS. 1A-C, Lateral movements of the arms 130a, 130b and the second arms 135a, 135b are controlled by movements of control wires 180a, 180b, 185a, 185b, respectively. For example, control wire 180a is coupled with arm 130a. When the control wire 180a is pushed (away from the physician/operator/user), arm 130a is moved laterally relative to the body 105. In other example, control wire 185a is coupled with the second arm 135a. When the control wire 185a is pushed, the arm 135a is moved laterally relative to both the body 105 and arm 130a. In a preferred embodiment, movement of each control wire is independent from movement of other control wires, and the movement of each arm or second arm is independent from other arms or second arms.

In some embodiments, once the control wires 180a, 180b, 185a, 185b moves the arms 130a, 130b, or the second arms 135a, 135b, the positions of at least one of those arms 130a, 130b, 135a, 135b, can be locked. For example, the control wires 180a, 180b, 185a, 185b can be held at one or more holders placed in the lumen 120 of the suturing device 100.

Figure 3:
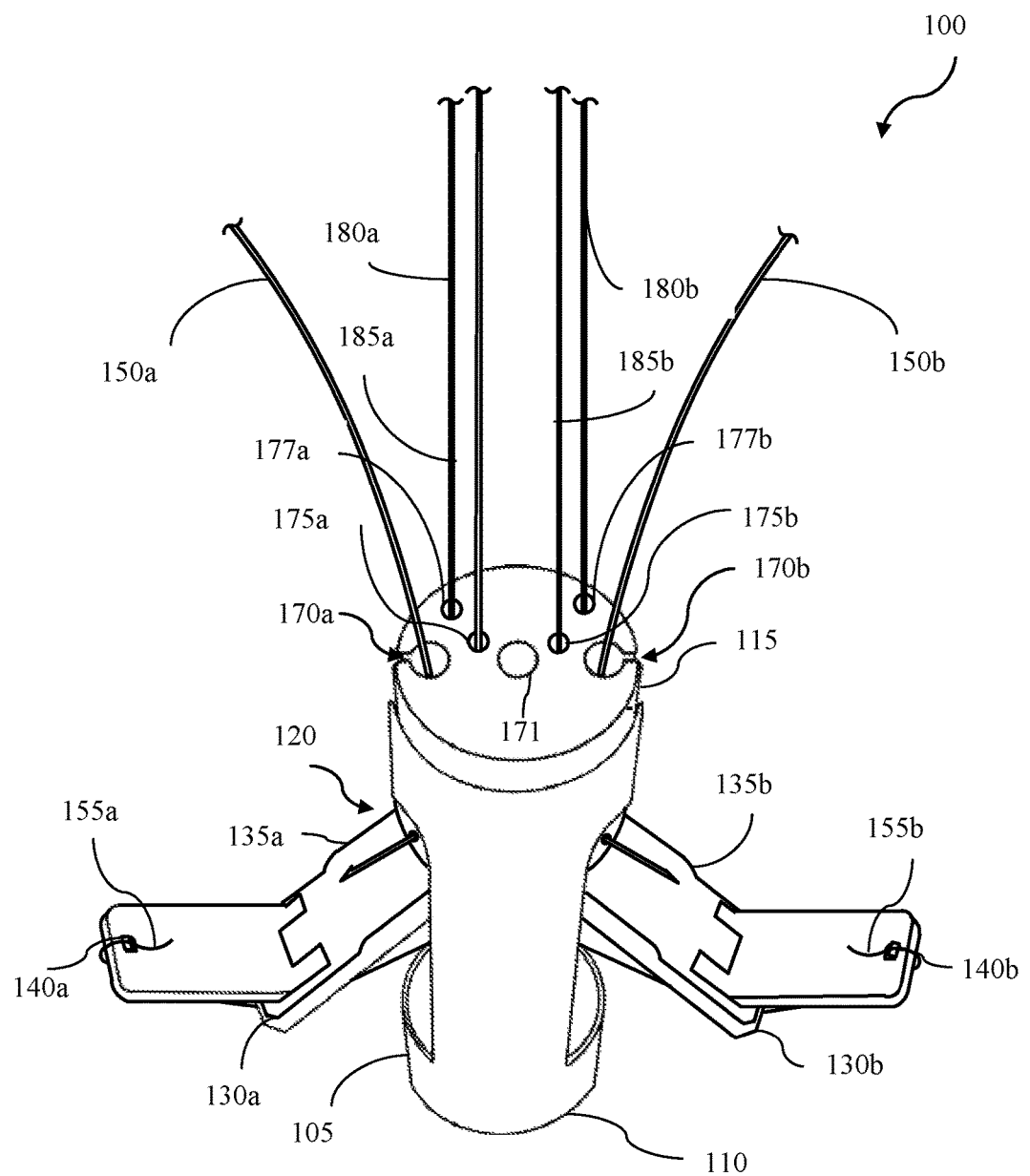
FIG. 3 illustrates another perspective view of the distal portion of suturing device of FIGS. 1A-C in an open configuration.

FIG. 3 shows another perspective view of the distal portion of suturing device 100 of FIGS. 1A-C and FIG. 2, in a substantially open configuration. As shown in FIG. 3, the control wires 180a, 180b, 185a, 185b separately enter lumen 120 of the distal portion of suturing device 100 via separate openings 175a, 175b, 177a, 177b. Separation of the control wires 180a, 180b, 185a, 185b allows for their independent operations without disturbing other control wires, so that angles of each arms 130a, 130b, or second arms 135a, 135b can be independently controlled. Preferably, needles 150a, 150b separately enter the lumen 120 via separate openings 170a, 170b. In some embodiments, the body 105 includes an additional opening 171 for a guide wire (not shown).

Because the catch targets 140a, 140b are coupled with the second arms 135a, 135b and then the arms 130a, 130b, lateral movement of the arms 130a, 130b and/or the second arms 135a, 135b away from the body 105 will automatically move the catch targets 140a, 140b away from the body 105. As the catch targets 140a, 140b are moved away in different angles, the corresponding needles 150a, 150b must also be reoriented to catch the sutures 155a, 155b coupled to the catch targets 140a, 140b. In preferred embodiments, this is accomplished by pivoting the needle guides 190a, 190b along with corresponding pivoting of the 130a, 130b.

Figure 4:
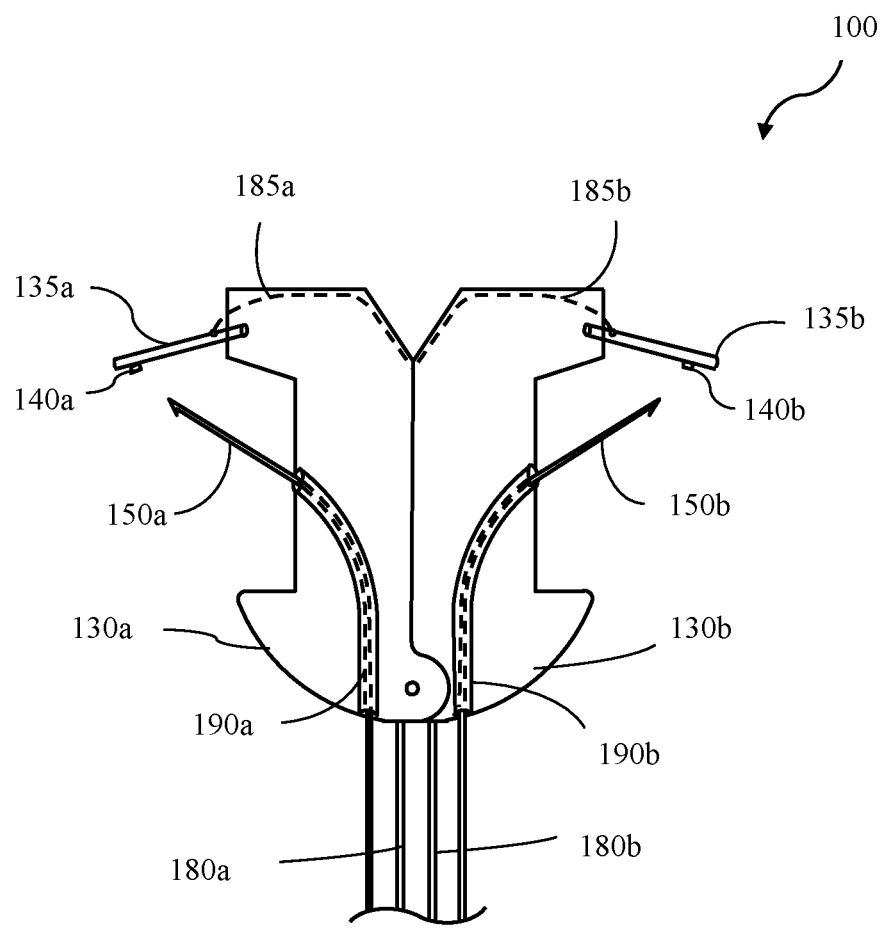
FIG. 4 illustrates a schematic view of a controlling mechanism of the distal portion of suturing device of FIGS. 1A-C.

FIG. 4 shows an embodiment in which the needle guides 190a, 190b directly attached to the arms 130a, 130b, respectively. Thus, when the control wires 180a, 180b laterally move the arms 130a, 130b relative to the body 105, the needle guides 190a, 190b are oriented along corresponding directions and angles with the arms 130a, 130b.

In some embodiments, it is contemplated that the needle guides 190a, 190b are not operated by direct attachment to the arms 130a, 130b, but are operated indirectly through coupling to the control wires 180a, 180b. In these embodiments, the needle guides 190a, 190b can be attached to wing-like structures (not shown) that resemble the arms 130a, 130b, which are then attached to the control wires 180a, 180b. Movements of the wing-like structures are controlled by the control wires 180a, 180b, concurrently with movement of the arms 130a, 130b.

Figure 5:
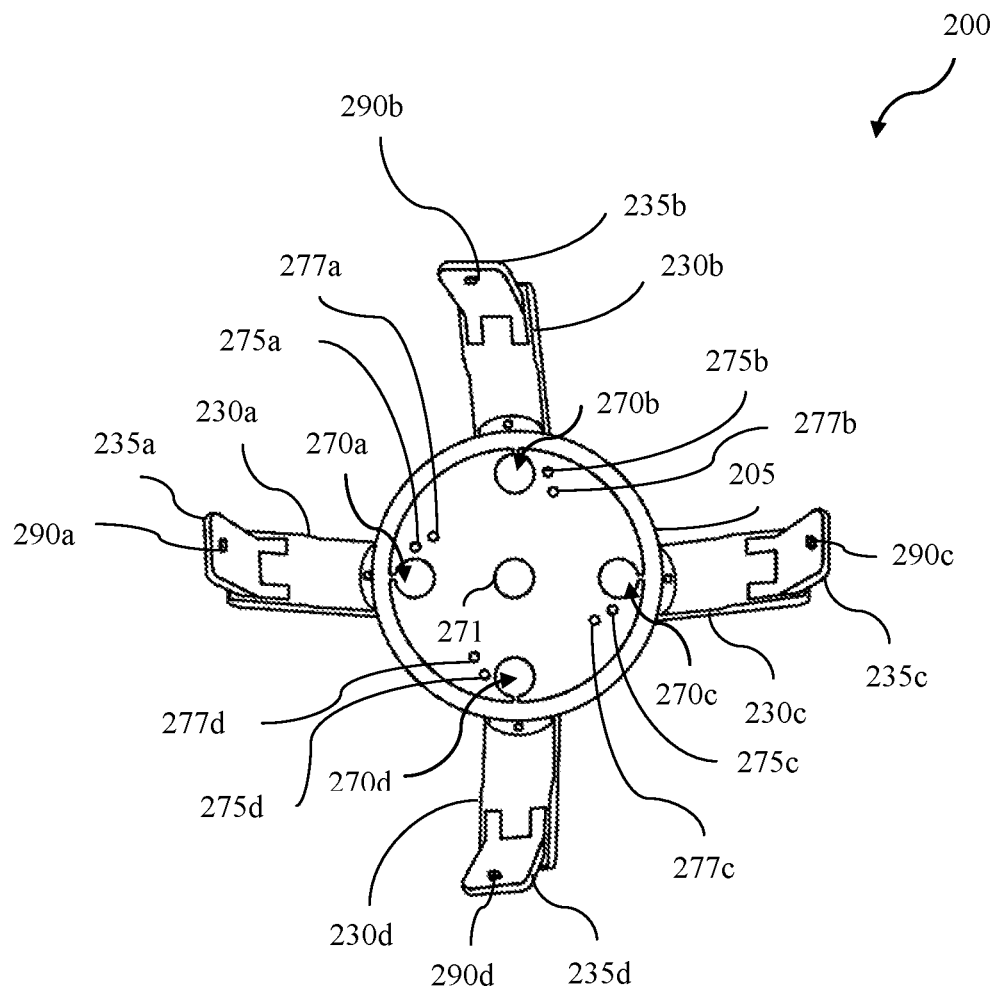
FIG. 5 illustrates a perspective underside view of another embodiment of the distal portion of suturing device in an open configuration.

FIG. 5 shows another embodiment of a distal portion of a suturing device 200, here displayed in a substantially open configuration. In this embodiment, the suturing device 200 includes four arms 230a, 230b, 230c, 230d, which are pivotally (hingeably) coupled with the body 205 of the suturing device 200. The distal portion of suturing device 200 further includes four second arms 235a, 235b, 235c, 235d, which are pivotally (hingeably) coupled with four arms 230a, 230b, 230c, 230d, respectively. In a preferred embodiment, the four arms 230a, 230b, 230c, 230d are radially arrayed about the body 205 of the suturing device 200 in circle.

Each of the arms 230a, 230b, 230c, 230d and each of the second arms 235a, 235b, 235c, 235d are controlled by control wires that are coupled with each of the arms 230a, 230b, 230c, 230d or each of the second arms 235a, 235b, 235c, 235d via separate openings 275a, 275b, 275c, 275d or 277a, 277b, 277c, 277d. The body 205 of the suturing device 200 also has needle openings 270a, 270b, 270c, 270d, through which each of the needles (not shown) passes, so that the needles can be directed toward catch targets 290a, 290b, 290c, 290d on the second arms 235a, 235b, 235c, 235d, respectively. Optionally, the body 205 of the suturing device 200 can have another opening 271 for a guide wire (not shown).

Another aspect of the invention includes methods of suturing various sizes of apertures in tissues, using the suture devices described in FIGS. 1-5. The methods generally include a step of providing a suture devices having at least one arm that is coupled with a catch target and a needle guide. As used herein, a step of providing includes a step of supplying, selling, or placing the device.

In a further step, a user can move the arm(s) using linear movements of the control wire(s) (e.g., pushing distally or pulling proximally), which move the target(s) away from or closer to the body, which thereby orients the needle guide(s) to direct the needle(s) towards the catch target(s). By automatically reorienting the direction of movement of the needle(s) along with reorientation of the arms, a physician/operator/user can suture multiple different sizes of apertures by moving the arm or arms of the suture device, without worrying about having the needle(s) properly reach the catch targets disposed on the arms.

Once the needle(s) are directed toward the corresponding catch target(s), the methods further include steps of moving the needle(s) toward the catch target(s), catching the suture(s), and moving the needle(s) with the suture(s) away from the catch target(s).

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A suturing device configured to suture various sizes of apertures, comprising:
    a body having a lumen, a proximal arm, and a distal arm, wherein a distal end of the proximal arm is pivotally coupled to a proximal end of the distal arm;
    a first control wire coupled with the proximal arm, and a second control wire coupled with the distal arm; and
    wherein movement of the first and second control wires moves the proximal and distal arms laterally and outwardly from the body.

2. The suturing device of claim 1, wherein the first and second control wires are independently moveable from each other.

3. The suturing device of claim 2, wherein movements of (a) the proximal arm and (b) the distal arm, by the first and second control wires, respectively, are independent from each other.

4. The suturing device of claim 1, further comprising a wire holder disposed inside the lumen, and at least one of the first and second control wires is coupled with the wire holder.

5. The suture device of claim 1, further comprising a first opening disposed inside the lumen, wherein the first opening is sized and dimensioned to receive the first control wire.

6. The suture device of claim 5, further comprising a second opening disposed inside the lumen, wherein the second opening is sized and dimensioned to receive the second control wire.

7. The suture device of claim 6, further comprising a suture needle and a third opening, and wherein the third opening is sized and dimensioned to receive the suture needle.

8. The suture device of claim 6, further comprising a guide wire and a fourth opening, and wherein the fourth opening is sized and dimensioned to receive the guide wire.

9. The suture device of claim 1, further comprising a needle guide coupled to the first proximal arm.

10. The suture device of claim 9, wherein the needle guide is coupled with at least one of the first and second control wires.

11. The suture device of claim 10, wherein the needle guide is configured to move in response to a movement of at least one of the first and second control wires.

12. The suture device of claim 9, wherein the needle guide is attached to the first arm.

13. A method of controlling a suturing device having an elongated body, a proximal arm, and a first distal arm, comprising:
    operating a first control wire to move the first proximal arm laterally and outwardly from the elongated body at a first angle;
    operating a second control wire to move the first distal arm laterally and outwardly from the first proximal arm;
    wherein the first and second control wires are independently moveable; and
    wherein a distal end of the first proximal arm is pivotally coupled to a proximal end of the first distal arm.

14. The method of claim 13, wherein the suturing device comprises a needle guide, the method further comprising moving the needle guide by moving at least one of the first and second control wires.

15. The method of claim 13, wherein the first and second control wires are configured to move the first proximal arm and the first distal arm at different angles.

16. The method of claim 13, moving the first distal arm comprises moving the first distal arm relative to the first proximal arm at a second angle.

17. The method of claim 13, further comprising locking a first control wire at a wire holder.

* * * * *